(12) United States Patent
Bitar

(10) Patent No.: US 12,251,366 B1
(45) Date of Patent: Mar. 18, 2025

(54) SULFORAPHANE-CYSTEINE FOR WOUND HEALING IN DIABETIC SUBJECTS

(71) Applicant: KUWAIT UNIVERSITY, Safat (KW)

(72) Inventor: Milad S. Bitar, Safat (KW)

(73) Assignee: KUWAIT UNIVERSITY, Safat (KW)

( * ) Notice: Subject to any disclaimer, the term of this patent is extended or adjusted under 35 U.S.C. 154(b) by 0 days.

(21) Appl. No.: 18/764,507

(22) Filed: Jul. 5, 2024

(51) Int. Cl.
  *A61K 31/198* (2006.01)
  *A61P 17/02* (2006.01)

(52) U.S. Cl.
  CPC ............ *A61K 31/198* (2013.01); *A61P 17/02* (2018.01)

(58) Field of Classification Search
  CPC .............................. A61K 31/198; A61P 17/02
  See application file for complete search history.

(56) References Cited

U.S. PATENT DOCUMENTS

2016/0250175 A1   9/2016   Cheng et al.

FOREIGN PATENT DOCUMENTS

| KR | 102167235 B1 | 10/2020 |
| WO | 2015002279 A1 | 1/2015 |
| WO | 2020060264 A1 | 3/2020 |

OTHER PUBLICATIONS

Zhou, Y., Wang, Y., Wu, S. et al. Sulforaphane-cysteine inhibited migration and invasion via enhancing mitophagosome fusion to lysosome in human glioblastoma cells. Cell Death Dis 11, 819 (Year: 2020).*

Department of Biochemistry and Molecular Biology, School of Basic Medical Sciences, Capital Medical University, "Sulforaphane-cysteine induces apoptosis by sustained activation of ERK1/2 and caspase 3 in human glioblastoma U373MG and U87MG cells", Oncol Rep., May 2017;37(5):2829-2838.

* cited by examiner

*Primary Examiner* — Sahar Javanmard
(74) *Attorney, Agent, or Firm* — Nath, Goldberg & Meyer; Joshua B. Goldberg

(57) ABSTRACT

A method of healing a wound in a patient, can include administering to a patient in need thereof a therapeutically effective amount of Sulforaphane-Cysteine (SFN-Cys). The therapeutically effective amount may be 1.5 μM. The SFN-Cys may be combined with an excipient and the excipient may be a poloxamer. The SFN-Cys, combined with a poloxamer, may be applied topically or taken orally.

9 Claims, 10 Drawing Sheets

SULFORAPHANE-CYSTEINE FOR WOUND HEALING IN DIABETIC SUBJECTS

BACKGROUND

1. Field

The present disclosure provides sulforaphane-cysteine as a treatment for inflammation and, more specifically, as a treatment for wounds in diabetic patients.

2. Description of the Related Art

Oxidative stress (OS) and inflammation are common features of clinical and experimental diabetes. These phenomena may be contributing factors for a number of chronic complications including insulin resistance, neuropathy, impaired wound healing, vascular dysfunction, atherosclerosis and more recently neurodegenerative diseases.

OS stems from an imbalance between levels of prooxidant molecules produced and the efficiency of a cellular endogenous system to detoxify and neutralize the reactive oxygen and nitrogen molecules. The main source of damage from OS is reactive oxygen species (ROS), free radicals having unpaired electrons that can induce inflammatory immune response concomitantly with oxidative modifications of key macromolecules including lipids, proteins, and nucleic acids. Consequently, death to dermal, neuronal, vascular, and cardiac cells may ensue.

Therefore, a treatment for reducing oxidative stress and inflammation to assist in wound healing is needed.

SUMMARY

The present subject matter relates to wound healing effects of sulforaphane-cysteine (SNF-Cys) as it relates to diabetes and other pathological states. As set forth herein, SNF-Cys was more efficacious than vascular endothelial growth factor (VEGF) in promoting tissue repair mechanisms in an animal model of type 2 diabetes.

In an embodiment, the present subject matter relates to a method of healing wounds in a patient, comprising administering to a patient in need thereof a therapeutically effective amount of Sulforaphane-Cysteine (SFN-Cys), having the formula:

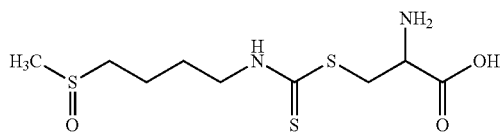 [SMILES: CS(=O)CCCCNC(=S)SCC(N)C(=O)O]

The present subject matter relates to a method of treating inflammation in a patient, comprising administering to a patient in need thereof a therapeutically effective amount of Sulforaphane-Cysteine (SFN-Cys).

These and other features of the present subject matter will become readily apparent upon further review of the following specification.

DETAILED DESCRIPTION OF THE PREFERRED EMBODIMENTS

Figure 1A:
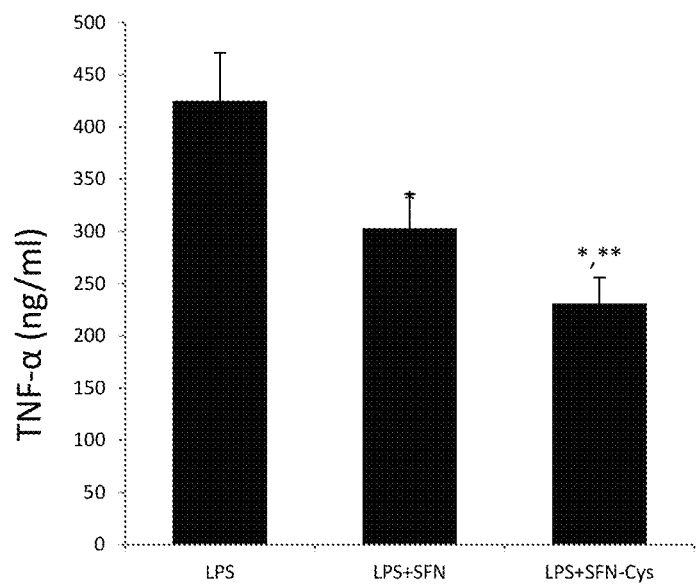
FIGS. 1A, 1B, 1C, and 1D are a series of graphs showing SFN-Cys suppressing the production of pro-inflammatory cytokines in LPS stimulated peritoneal macrophages in a mouse model of type 2 diabetes.

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as diabetic wounds and non-healing wounds associated with diabetes. Other conditions may include sarcopenia, fat grafting, psoriasis, nerve regeneration and diabetic neuropathy, and erectile dysfunction.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to the use of sulforaphane-cysteine (SNF-Cys) for treating inflammation, wounds associated with diabetes, and other pathological states.

Oxidative stress (OS) and inflammation are common features of clinical and experimental diabetes. These phenomena are contributing factors for a number of chronic complications including insulin resistance, neuropathy, impaired wound healing, vascular dysfunction, atherosclerosis and more recently neurodegenerative diseases. As described herein, sulforaphane-cysteine (SNF-Cys) demonstrated anti-inflammatory, antioxidant, and wound healing effects, In particular, data described in the examples herein support that SNF-Cys can have therapeutic potential in the treatment of non-healing diabetic wounds. SNF-Cys was more efficacious than vascular endothelial growth factor (VEGF) in promoting a tissue repair mechanism in an animal model of aged type 2 diabetes. The mechanisms responsible for this beneficial effect may be related to the favorable effect of SNF-Cys on TGF-β-Slug-vimentin-dependent signaling pathway. In this setting, it was confirmed that the gene expression of vimentin was markedly decreased in diabetic wound biopsies when compared to corresponding control values. A similar reduction in TGF-β-Slug signaling level was also evident in this disease state. Most interestingly, semi-chronic administration of SNF-Cys ameliorated both the deficit in Vimentin-TGF-β-Slug signaling and the impairment in wound healing during the course of diabetes.

The present inventors further demonstrated that SNF-Cys, at certain concentrations, protects neuronal, vascular, muscle, cardiac and stem cells from a heightened state of oxidative state and low-grade inflammation-induced apoptotic cell death. Thus, SNF-Cys may have a therapeutic benefit in the following conditions in addition to impaired wound healing: Sarcopenia, Fat grafting, Psoriasis, Nerve regeneration and diabetic neuropathy, Erectile dysfunction, and Cardiac fibrosis.

The present subject matter relates to a method of healing wounds in a patient, comprising administering to a patient in need thereof a therapeutically effective amount of Sulforaphane-Cysteine (SFN-Cys), having the formula:

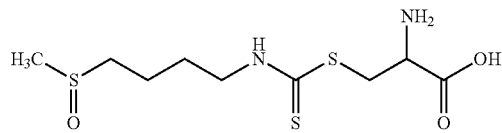 [SMILES: CS(=O)CCCCNC(=S)SCC(N)C(=O)O]

In various embodiments, the therapeutically effective amount may be about 1.5 μM.

In other embodiments, the SFN-Cys may be combined with an excipient. In various embodiments, the excipient may be a biomedical polymer. In still other embodiments, the excipient may be a poloxamer. Poloxamers, are a class of synthetic block copolymers which consist of hydrophilic poly(ethylene oxide) (PEO) and hydrophobic poly(propylene oxide) (PPO), arranged in an A-B-A triblock structure. In various embodiments, the poloxamer may be Pluronic® acid (Pluronic is a registered trademark of BASF CORPORATION a CORPORATION; DELAWARE, USA). In some embodiments, the SFN-Cys, including the poloxamer, may be applied topically. In further embodiments, the SFN-Cys may be combined with other emulsifying agents, solubilizing agents, surfactants, and/or wetting agents.

In various embodiments of the method described herein, the patient may have diabetes.

In some embodiments, the SFN-Cys combined with poloxamers may be administered orally.

In other embodiments, the method includes administering the therapeutically effective amount daily.

In various embodiments, the therapeutically effective amount may be in the range of 17-25 mg per 70 kg of the patient.

In an embodiment, a method of treating inflammation in a patient can include administering to a patient in need thereof a therapeutically effective amount of Sulforaphane-Cysteine (SFN-Cys), having the formula:

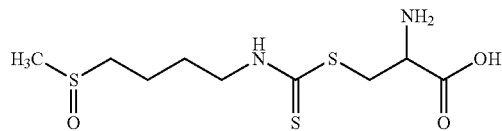 [SMILES: CS(=O)CCCCNC(=S)SCC(N)C(=O)O]

The following examples relate to various methods of manufacturing certain specific compounds as described herein. All compound numbers expressed herein are with reference to the synthetic pathway figures shown above.

EXAMPLES

Example 1

Anti-Inflammatory Activity

Figure 1B:
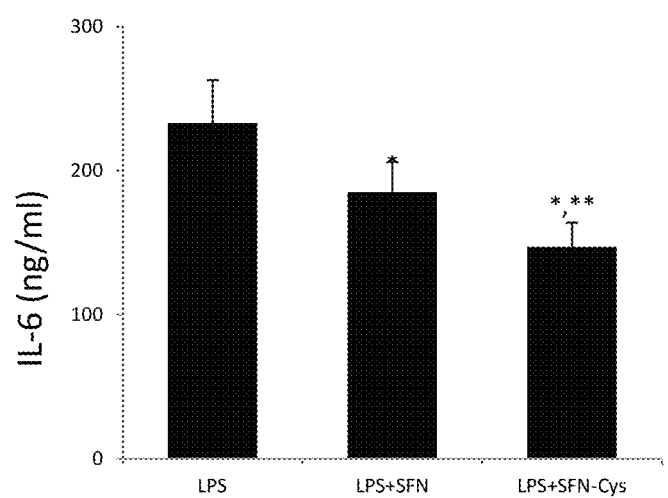

Sulforaphane (SFN) or Sulforaphane-Cysteine (SFN-Cys) both exhibited anti-inflammatory and antioxidant activities in a mouse model of type 2 diabetes. This was exemplified in the current study by the ability of SFN-CYS to inhibit lipopolysaccharide (LPS)-induced peritoneal macrophages and bone marrow-derived macrophages to produce tumor necrosis factor-α (TNF-α) and interlukin-6 (IL-6). TNF-α and IL-6 are two of the major inflammatory mediators that contribute to the pathogenesis of low-grade inflammation; a phenomenon which is commonly associated with the diabetic state. In this context, using ELISA- or RT-PCR-based technique, it was found that 6 hours of exposure to LPS led to increased levels of TNF-α and IL-6 as shown in the graphs of FIGS. 1A and 1B. Pre-treatment with SFN-Cys inhibited the expression of LPS-induced TNF-α and IL-6 protein at a therapeutic dose of 1.5 µM (FIGS. 1A and 1B).

Figure 1C:
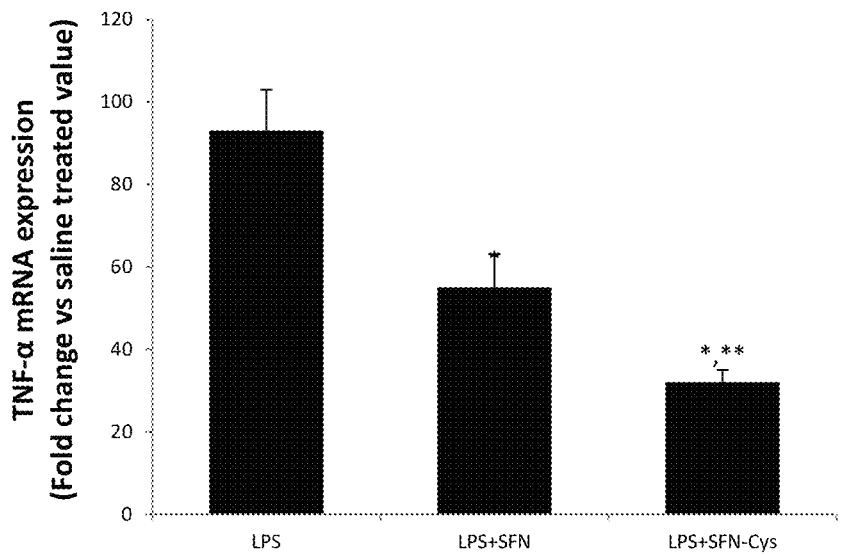
Figure 1D:
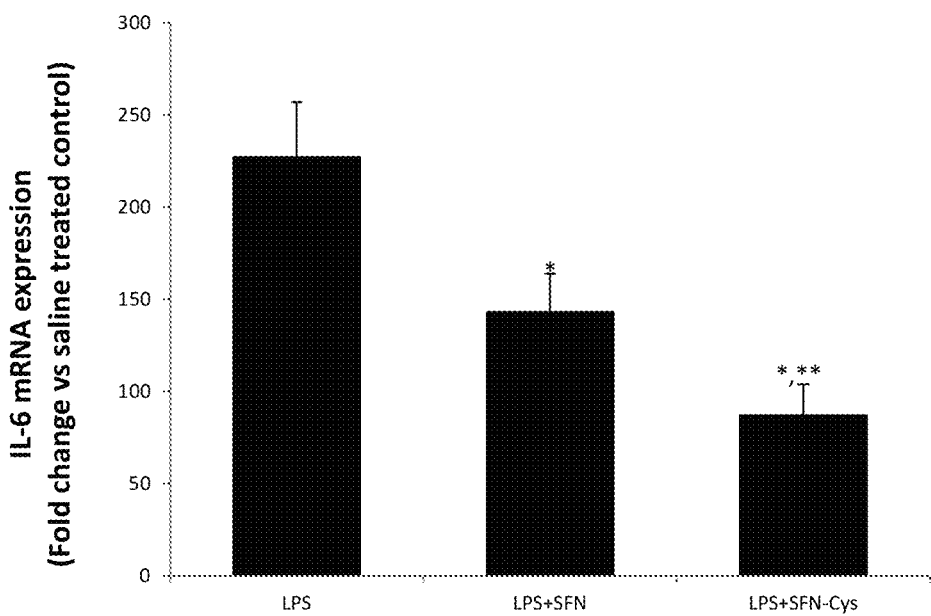

Additional tests were conducted to determine whether SFN-Cys also suppresses TNF-α and IL-6 expression at the mRNA level. The results revealed that SFN-Cys significantly inhibited LPS-induced mRNA up-regulation of both cytokines, as illustrated in the graphs in FIGS. 1C and 1D. It is worth noting that this effect of SFN-Cys is not unique to peritoneal macrophages since analogous results were also seen in bone marrow-derived macrophages. Together these findings confirm that SFN-Cys has powerful anti-inflammatory activity and appears to be more potent than SFN in this regard.

Example 2

Antioxidant Activity

Figure 2A:
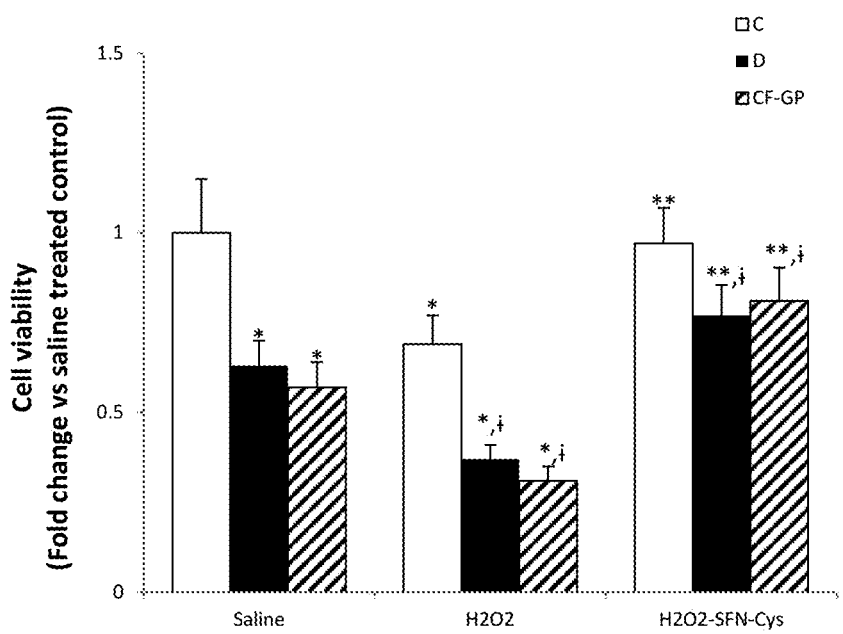
FIGS. 2A, 2B, 2C, and 2D are a series of graphs showing the antioxidant activity of SFN-Cys in fibroblasts derived from control and diabetic wounds.

To determine if SFN-Cys is involved in cellular detoxification of oxidant load, wound fibroblasts derived from the granulation tissue of control and diabetic animals with $H_2O_2$ were measured for their abilities to survive acute oxidative stress in the presence or absence of SFN-Cys. Diabetic fibroblasts (DF) were significantly more sensitive to this form of oxidative stress compared with control fibroblast (CF) as illustrated in FIG. 2A. Moreover, CF exposed for 72 hours to high glucose (25 mmole/L and palmitate 200 µmole/L, CF-GP) to mimic the diabetic state produced analogous results to those seen with DF as illustrated in FIG. 2A. Supplementing DF and CF-GP with SFN-Cys at a dose of 1.5 to 5 µM eliminated the reactive oxygen species difference between these cells and enhanced DF and CF-GP resistance to $H_2O_2$ (FIG. 2A).

Figure 2B:
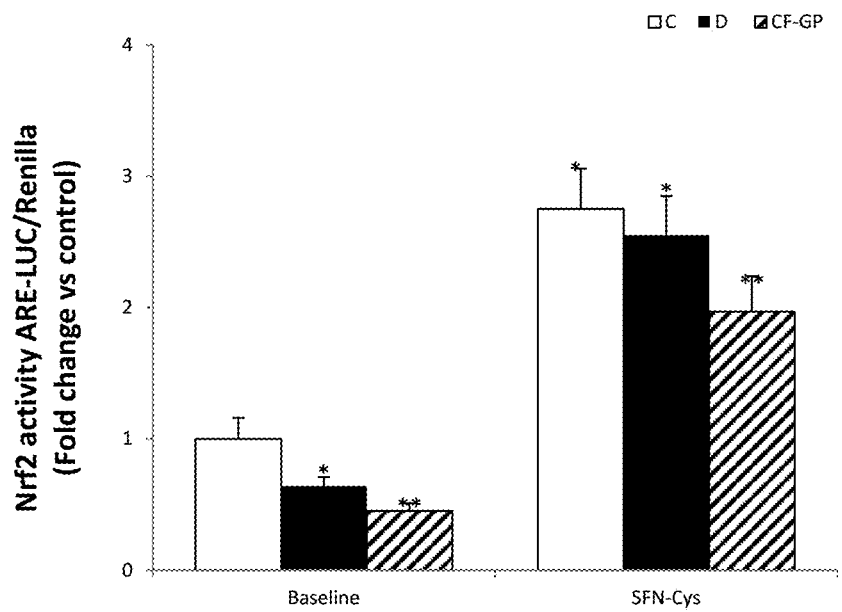
Figure 2C:
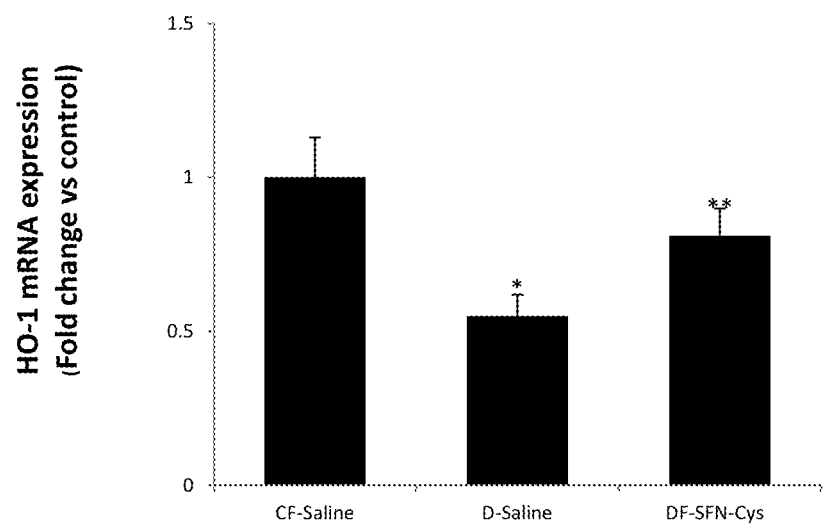
Figure 2D:
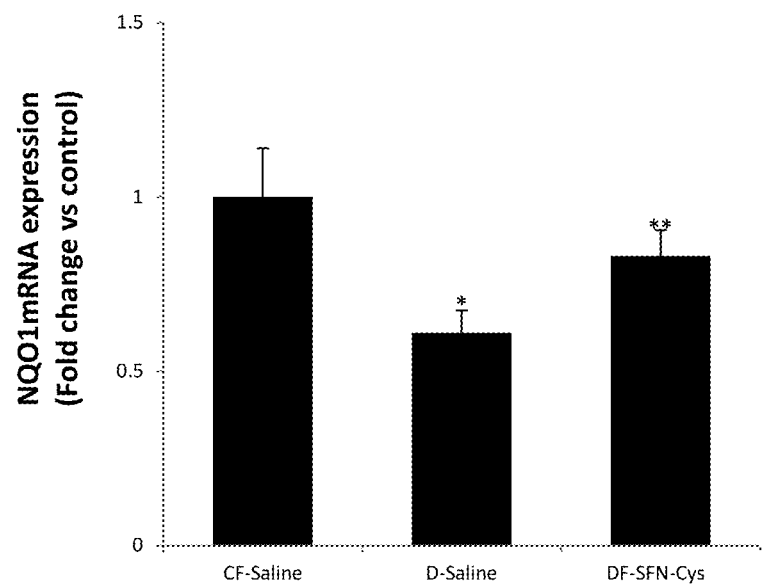

To better characterize how SFN-Cys impacts cellular antioxidant levels, the ability of SFN-Cys to regulate the transcription factor nuclear factor erythroid 2-related factor 2 (Nrf2) was assessed, which is a master regulator of the antioxidative stress response that induces the expression of antioxidant proteins such as heme oxygenase (HO) and NAD(P)H dehydrogenase (quinine; NQO1) and key enzymes in the glutathione system. In this context, Nrf2 transcriptional activity was first measured using a vector encoding luciferase driven by the NQO1 promoter. Nrf2 was markedly reduced in DF and CF-GP compared with control counterparts as illustrated in FIG. 2B. Moreover, the mRNA expression of the NRF2 target genes including NQO1 and HO was also reduced as a function of diabetes, as illustrated in FIGS. 2C and 2D. Administration of SNF-Cyst at the above indicated concentration (1.5 µM, the lowest effective concentration) ameliorated diabetes-induced suppression of the Nrf2 activity and Nrf2-target genes including HO and NQO1 (FIG. 2A-D). Overall, the above data gives credence to the concept that SNF-Cys exhibits powerful anti-oxidant and anti-inflammatory activities.

Example 3

Enhancement of Wound Healing and Tissue Repair

Figure 3A:
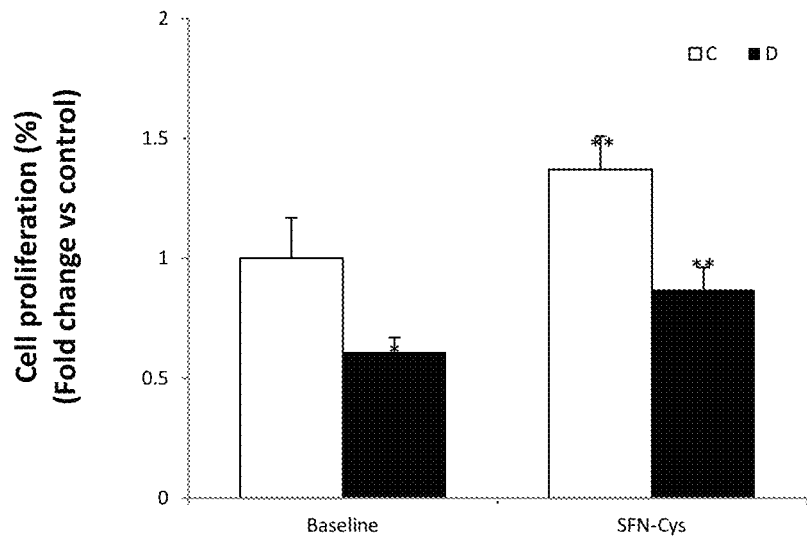
FIGS. 3A, 3B, 3C, 3D, and 3E are a series of graphs showing the wound healing potential of SFN-Cys both in vitro and in vivo.
Figure 3B:
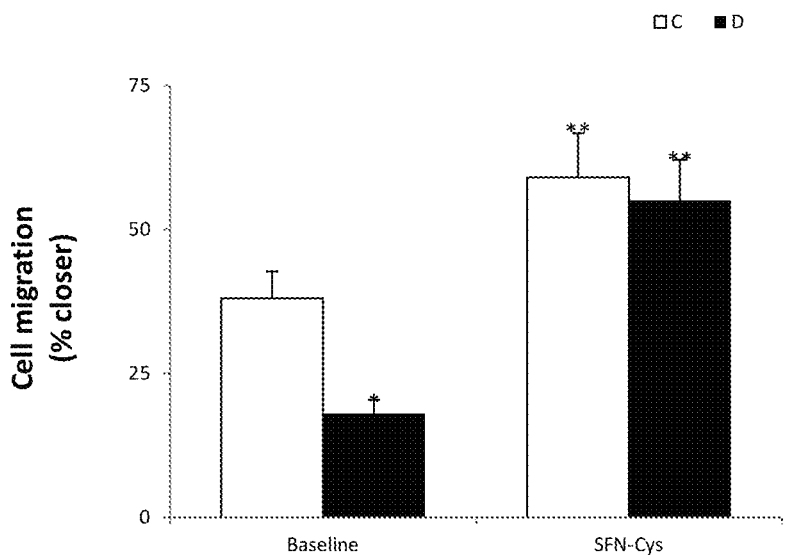
Figure 3C:
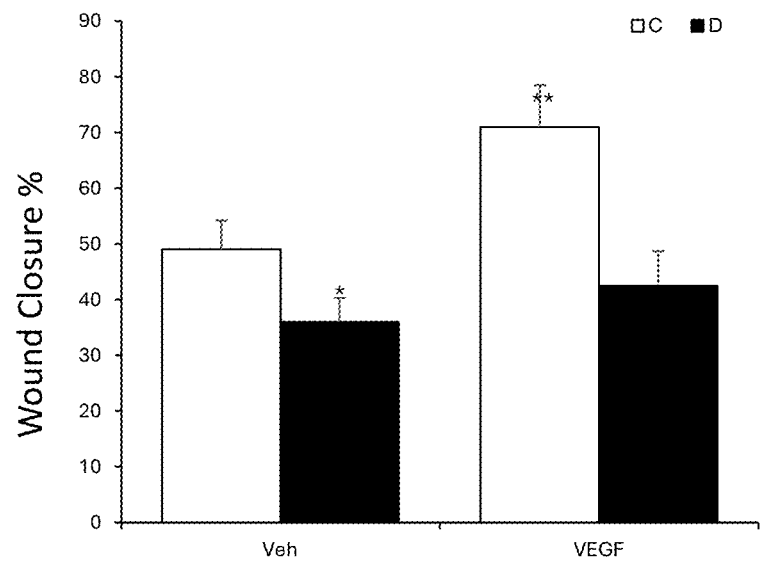
Figure 3D:
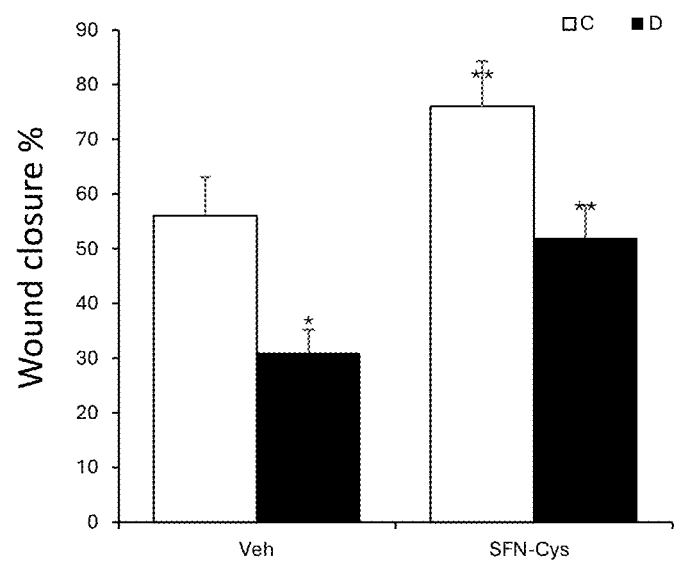
Figure 3E:
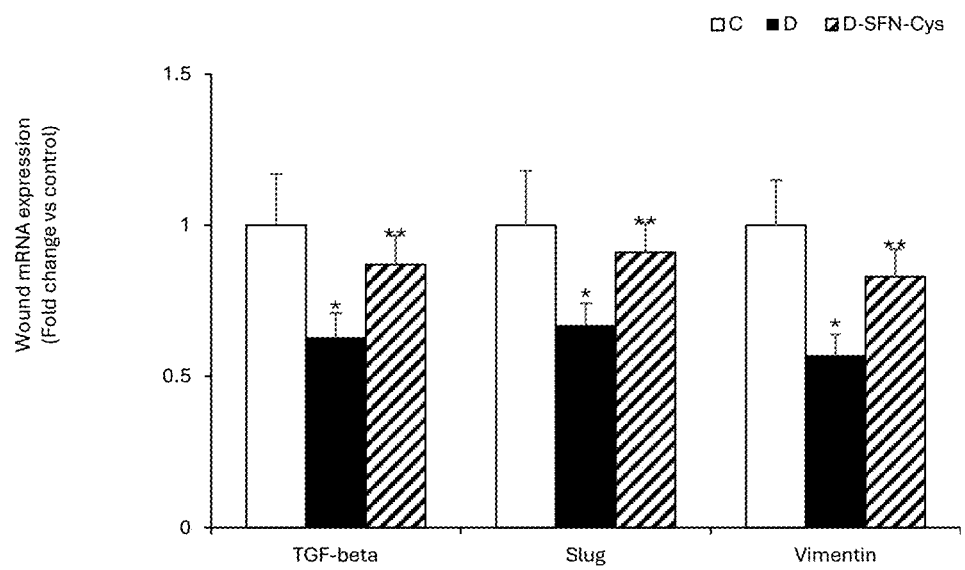

Successful wound healing necessitates a series of tightly coordinated and overlapping processes including inflammation, new tissue formation and remodeling. Fibroblasts, in response to growth factors-released mostly by macrophages, migrate to the site of injury, where they proliferate and lay down the extracellular matrix (ECM). Consequently, this facilitates cell migration and tissue reconstruction. The effect of a therapeutic concentration of SFN-Cys (1.5 µM) was investigated on the proliferation of fibroblasts isolated from the granulation tissue of control and diabetic wounds. Similarly, the effect of SFN-Cys on cell migration in the in vitro wound closure assay was also considered. The results revealed that SFN-Cys at the above indicated concentration enhanced cell proliferation in both CF and DF (FIG. 3A). Moreover, it was found that the migration of DF for 24-hours was markedly decreased compared with the corresponding control values (FIG. 3B). Interestingly, SFN-Cys enhanced cell migration not only in control but also in diabetic fibroblasts (FIG. 3B). Indeed, the percentage of increase in cell migration in response to SFN-Cys was greater in diabetics as compared to controls under the same experimental condition. These data point to the possibility that SFN-Cyst may be of value in non-healing diabetic wounds. Accordingly, in vivo wound closure properties of SFN-Cys were examined using an excisional wound healing rat model. SFN-Cys containing Pluronic acid was topically applied to the wound at a dose of 1.5 µmol concentration and the wound closure area was digitally photographed and quantified. Digital photographs were obtained on day-0 through day-7 of post wounding. The data clearly indicated that diabetic wounds healed at a much slower rate than that of controls (FIG. 3C). It is worthy to note that SFN-Cys enhanced wound closure. In this context, the wound healing time-course was faster in SFN-Cys containing Pluronic acid than the Pluronic acid alone (FIG. 3C). Most interestingly, the data confirmed that SFN-Cys is better than vascular endothelial growth factor (VEGF) in mitigating diabetes-related impairment of wound healing (FIG. 3D). VEGF is a well-established enhancer of the proliferative phase of healing.

Although the molecular mechanism by which SFN-Cyst enhanced wound healing potential was not fully explored in this study, it is possible to involve the Vimentin-TGF-β-Slug signaling pathway. Vimentin is an intermediate filament protein that participates in several cellular processes essential for wound healing, including cell proliferation, adhesion, migration and cytoskeletal rearrangement. Moreover, vimentin also amplifies epithelial-mesenchymal-transition via enhancing TGF-β-Slug signaling. It was determined that gene expression of vimentin was markedly decreased in diabetic wound biopsies when compared to corresponding control values (FIG. 3D). A similar reduction in TGF-β-Slug signaling level was also evident in this disease state (FIG.

3D). Most interestingly, semi-chronic administration of SFN-Cys ameliorated both the deficit in Vimentin-TGF-β-Slug signaling and the impairment in wound healing during the course of diabetes.

Taken together, the data provides evidence that SFN-Cys increases wound healing potential both in control and diabetic subjects, possibly via augmenting Vimentin-TGF-β-Slug signaling pathway.

Example 4

Pharmacodynamics and Toxicodynamic Properties of SFN-Cys

Testing the pharmacodynamic and toxicodynamic properties of SFN-Cys dictated the mixing SFN-Cys with a powdered diet. The estimated dose delivered by this diet was 1.5-2.5 μmol/mouse (n=4). The SFN-Cys diet was stored at 4° C. and the feeders were refilled daily for the duration of the study (21 days). Corresponding animals received food without the drug. It was found that the mRNA expression of heme oxygenase and NQO1 measured in different tissues including heart, kidney, liver and skin was increased in response to SFN-Cys feeding by about 3 folds relative to corresponding control values.

Next, a toxicity assessment of chronically administered SFN-Cys revealed no obvious signs of adverse effect as judged by the similarity in body weight (control, 21.5±3; control-SFN-Cys, 22.7±3.2) and behavior. To strengthen this conclusion, extensive measurements were conducted on plasma levels of key parameters of kidney and liver toxicities in addition to the lipid and carbohydrate profiles. The data regarding these studies are outlined in Table 1.

TABLE 1

Toxicodynamic/Pharmacodynamics properties of SFN-Cys in mice

| Plasma test | Control-diet | SFN-Cys-diet |
|---|---|---|
| Glucose (mmol/L) | 6.7 ± 0.97 | 5.87 ± 0.90 |
| Triglyceride (mmol/L) | 1.21 ± 0.23 | 1.15 ± 0.25 |
| Free fatty acid (mmol/L) | 0.47 ± 0.10 | 0.41 ± 0.14 |
| Total cholesterol (mmol/L) | 2.35 ± 0.37 | 2.15 ± 0.42 |
| Total bilirubin (μmol/L) | 4.87 ± 0.68 | 4.23 ± 0.48 |
| Creatinine (μmol/L) | 9.37 ± 0.96 | 8.87 ± 0.91 |
| Alkaline phosphatase (IU/L) | 47.8 ± 17 | 27 ± 15 |
| Alanine aminotransferase (IU/L) | 51.7 ± 21 | 44.5 ± 17 |
| Aspartate aminotransferase (IU/L) | 167 ± 21 | 172 ± 25 |
| Ketone bodies (mmol/L) | 0.087 ± 0.017 | 0.079 ± 0.01 |

Example 5

Pharmacodynamics and Toxicodynamic Properties of SFN-Cys

Figure 4A:
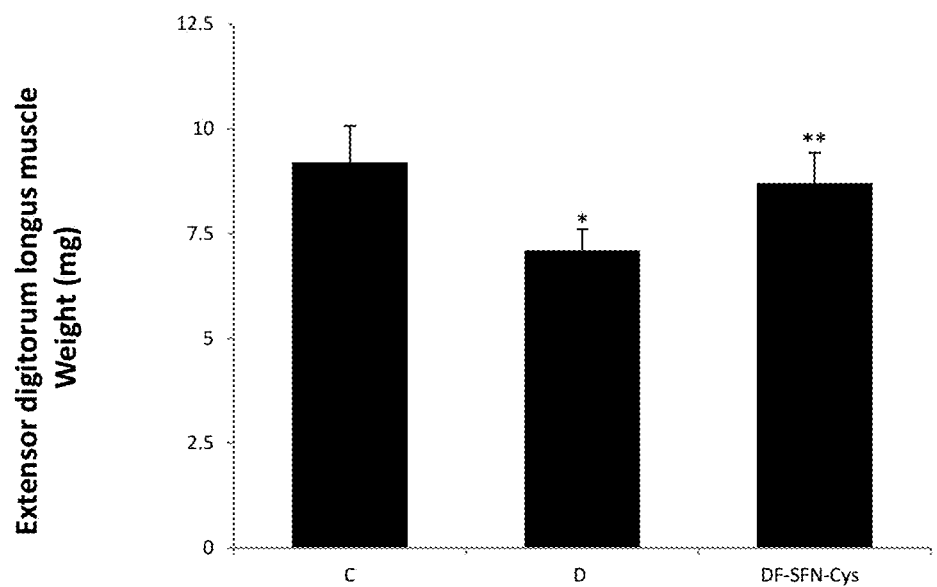
FIGS. 4A, 4B, 4C, 4D, 4E, and 4F are a series of graphs showing SFN-Cys effect on muscle weights, nitric oxide production and pain threshold in animal models of type 2 diabetes.
Figure 4B:
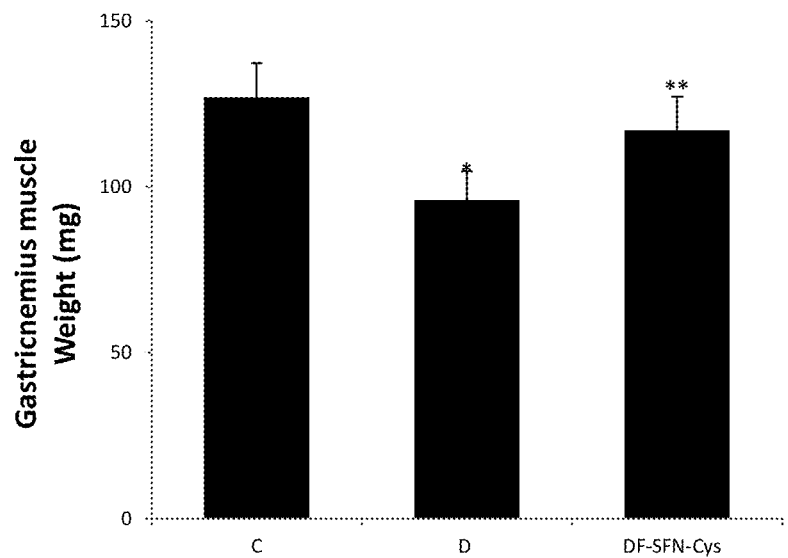
Figure 4C:
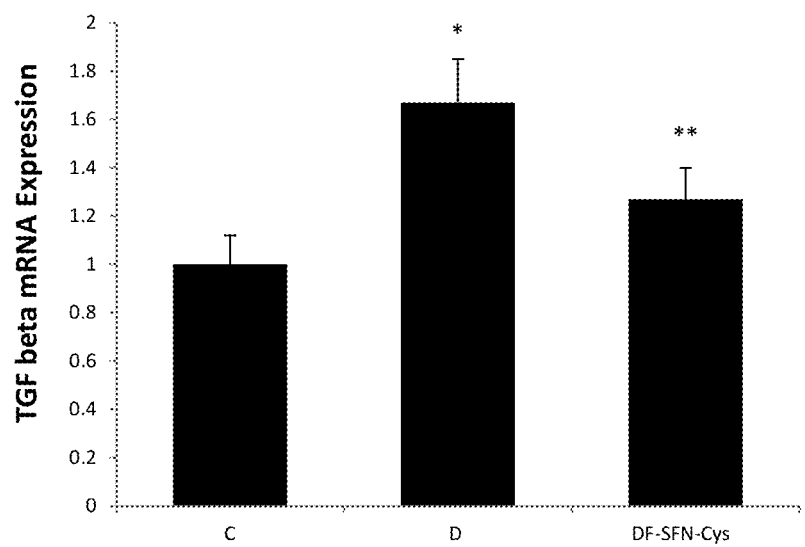
Figure 4D:
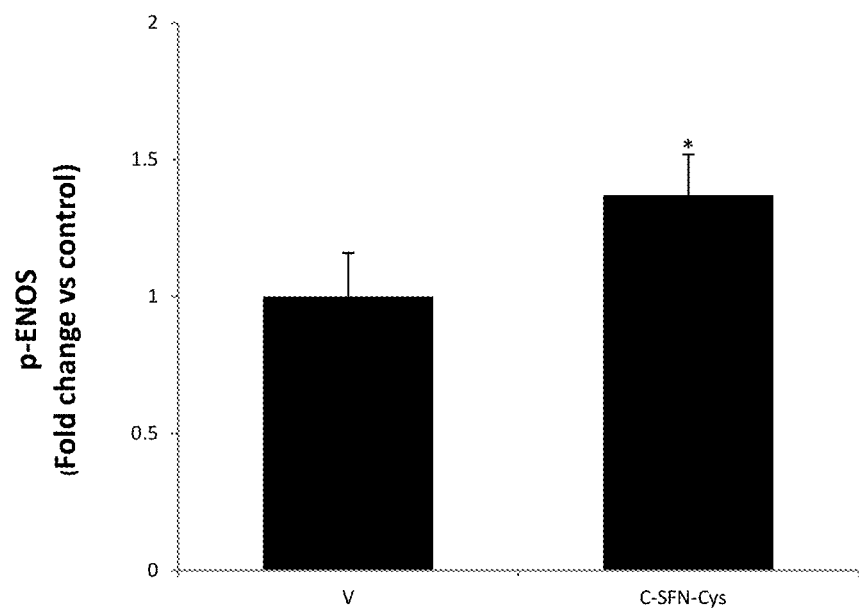
Figure 4E:
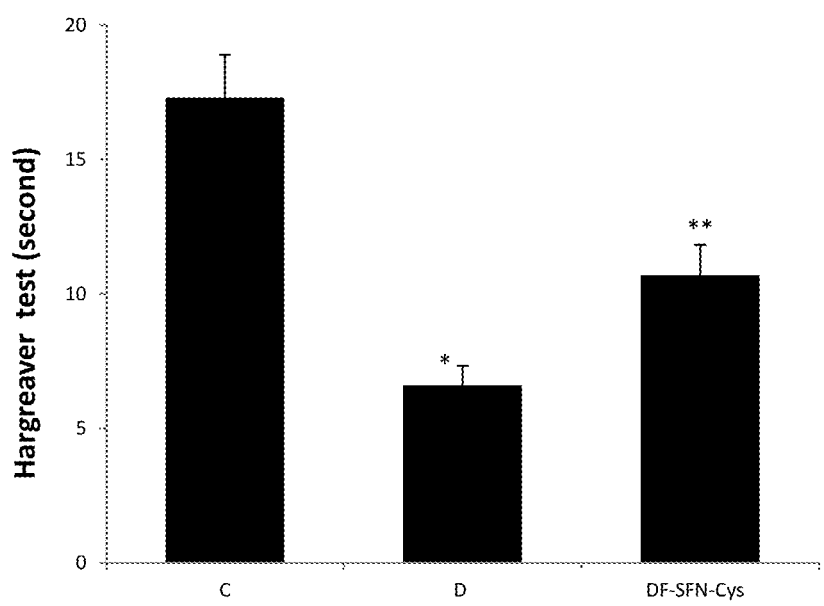
Figure 4F:
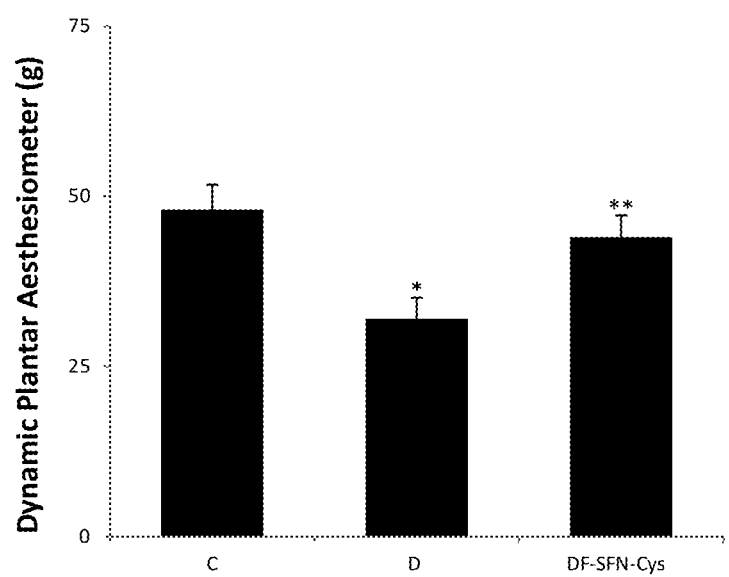

Therapeutic rational was considered for SFN-Cys effectiveness in the following pathological conditions: Sarcopenia-SFN-Cys increased muscle weight in diabetic mice, see FIGS. 4A and 4B; Cardiac fibrosis-SFN-Cys inhibits transforming growth factor beta (TGF-β) expression, see FIG. 4C; Erectile dysfunction-SFN-Cys increased endothelial nitric oxide activity and expression in corpus cavernosum. This enzyme is responsible for the production of nitric oxide, the most potent vasodilator known at the present, see FIG. 4D; Diabetic neuropathy-SFN-Cys elevated pain threshold in diabetic rats when administered at a dose of 5 μmol/rat, see FIGS. 4E and 4F.

Example 5

Materials and Methods

Animal and Treatments

C57BL mice were obtained from Kuwait University Laboratory Animals (Kuwait). Type II diabetic Goto Kakazaki (GK) rats were produced by selective inbreeding of glucose-intolerant Wistar rats. All offsprings of GK animals were similarly affected by mild hyperglycemia within the first two weeks after birth. In 1996, a colony of GK rats at Kuwait University was initiated, from breeding stock kindly provided by Dr. Samy Abdel Halim (Karolinska Institute, Sweden). Weight matched Wistar rats served as control (Kuwait University breeding colony). All animal experiments were conducted in accordance with the National Institutes of Health Guide for the Care and Use of Laboratory Animals with the approval of the Scientific Investigation Board of Kuwait University. Animals were maintained on a 12-h light/12-h dark cycle with free access to water and a pelleted diet. All animals were female, 8-10 weeks of age equally distributed between control and the treated groups.

For dietary treatment with SFN-Cys, the SFN-Cys was mixed with a powdered diet (7.5 mg of SFN-Cys per kg of food). The estimated dose delivered by this diet was about 1.0-1.5 mg/kg. The diet was stored at 4° C. and the feeders were refilled daily. Control animals received diet alone. Body weights were recorded twice a week and at the termination of the study, blood was drawn in EDTA-containing tubes, plasma was collected by centrifugation and stored at −80° C. until analysis.

Fibroblast Cell Line

Control and diabetic fibroblasts were isolated from wounds inflicted on control Wistar rats (CF) or Goto kakazaki rats (GK), a model of non-obese type 2 diabetes. All information regarding the GK rats and the preparation and culturing of control (CF) and diabetic (DF) fibroblasts was described in detailed in previous publications, Bitar, M S, and Mulla, F. Am J Phyaiol. 301: E119, 2011; Bitar M S and Mulla, F. Dis Mod. Mech. 5: 375, 2012.

Macrophage Cell Culture

Thioglycollate-elicited mouse peritoneal macrophages were prepared from C57BL (8-10 weeks old) and cultured in RPMI 1640 with 10% (v/v) FCS Bone marrow-derived macrophages were generated in RPMI medium containing M-CSF (10 ng/mL) according to previously published procedure. For cytokine ELISA assay, cells were seeded at $5 \times 10^5$ in 12-well plates, whereas for mRNA expression, the cells were seeded at 2×10. LPS and used at a dose of 100 ng/mL. Similarly. SFN-Cys was used at a concentration of 1.5 umol/L.

In Vivo Wound Closure Assay

For wounding experiments, 15-18-month female GK rats were anesthetized with intraperitoneal injection of ketamine/xylazine and full-thickness wounds were made in the mid dorsal skin with 8-mm disposable punches. To evaluate the effect of SFN-Cys on wound closure, the drug was dissolved initially with DMSO and then diluted with a 25% Pluronic acid solution at a dose of 1.5 μmol/wound; applied topically to the wound every other day. The wounds were photographed at 0-, 3- or 7-days post-wounding.

In Vitro Wound Healing Repair Assay

Fibroblasts ($1 \times 10^5$/well) were cultured until confluence. The monolayers were wounded using 200 μL micropipette tip, washed with PBS and incubated with 1.5 μM with SFN-Cys for 24 hrs. The cultures were subsequently photographed using a phase-contrast microscope to monitor the migration of cells into the wounded area. The closure of the wounded area was calculated using Image J software (NIH). Data are expressed as a percent of wound closure.

Cell Viability Assay

The response of CF and DF to $H_2O_2$ cytotoxicity was measured by seeding the cells into 96-well plates at a density of $5\times10^3$ to $8\times10^3$ cells per well and were allowed to adhere overnight in 10% FCS-DMEM medium. Thereafter, they were treated with $H_2O_2$ at a concentration of 400 μmol/L for 4 hours. Cell viability was measured using WST-1 (Dojindo, USA;) according to the manufacturer's instructions.

Real-Time PCR for mRNA Quantitation

Total RNA from cells or frozen sponge implants was extracted using the Trizol reagent (Invitrogen), and the RNA integrity was verified by agarose gel electrophoresis. Approximately 1 μg of RNA was reverse transcribed (Superscript II Reverse Transcriptase Kit, Invitrogen) and amplified using the TaqMan Assay on Demand (Applied Biosystems) in a 25 μL reaction volume containing two unlabeled primers, a 6-carboxyfluorescien-labeled TaqMan MGB probe and the master mix. The amplified sequences were assessed using the ABI 7500 Prism Sequence Detection system machine. The results were expressed as mRNA levels normalized to 18S or GAPDH in each sample.

Cell Transfection and Nrf2 Activity (NQO1-ARE Activity)

CF and DF were transfected with the antioxidative stress response element ARE-luciferase and pRenilla vectors using lipofectamine 2000 (Invitogen, USA). In this context, cells were plated and transfected in 12-well plates. Following treatment with SFN-Cys, cells were lysed and firefly and Renilla luciferase activity was determined using Dual luciferase assay (Promega, USA).

Cytokine ELISA

For cytokine ELISA, supernatants from cultured macrophages were collected in response to treatment with SFN and SFN-Cys for 6 h. The total TNF-α and TL-6 were measured by enzyme-linked immunosorbent assay (ELISA) using kits (R&D system, USA) according to the manufacturer's protocols.

Blood Tests

Blood tests were performed on hemolysis free plasma samples obtained from animals receiving 21 days of a normal diet or a diet containing 7.5 mg/kg food of SFN-Cys using commercially available kits.

Statistical Analysis

Data are expressed as the means±SEM. Comparisons were made by two-tailed paired Student's t-test or by one-way analysis of variance followed by Bonferroni post hoc test. A level of P≤0.05 was considered to be significant.

It is to be understood that the method of using SFN-Cys for treatment of non-healing wounds and inflammation is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

The invention claimed is:

1. A method of healing a wound in a patient, comprising administering to a patient in need thereof a therapeutically effective amount of Sulforaphane-Cysteine (SFN-Cys), having the formula:

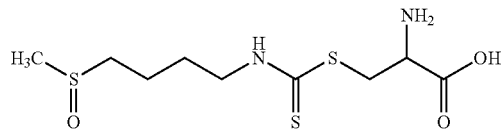 [SMILES: CS(=O)CCCCNC(=S)SCC(N)C(=O)O]

2. The method of claim 1, wherein the therapeutically effective amount is 1.5 μM.

3. The method of claim 1, wherein the SFN-Cys is combined with an excipient.

4. The method of claim 3, wherein the excipient is a poloxamer.

5. The method of claim 4, wherein the SFN-Cys combined with the poloxamer is applied topically.

6. The method of claim 1, wherein the patient has diabetes.

7. The method of claim 4, wherein the SFN-Cys combined with the poloxamer is administered orally.

8. The method of claim 1, wherein the method comprises administering the therapeutically effective amount daily.

9. The method of claim 8, wherein the therapeutically effective amount is in the range of 17 to 25 mg per 70 kg of the patient.

* * * * *